United States Patent
Mizukusa et al.

(10) Patent No.: US 6,893,128 B2
(45) Date of Patent: May 17, 2005

(54) UNIT FOR OBTAINING AND DISPLAYING FUNDUS IMAGE

(75) Inventors: Yutaka Mizukusa, Shizuoka-ken (JP); Akihiro Fujita, Mie-ken (JP)

(73) Assignee: Kowa Company, Ltd., Aichi-Ken (JP)

( * ) Notice: Subject to any disclaimer, the term of this patent is extended or adjusted under 35 U.S.C. 154(b) by 408 days.

(21) Appl. No.: 10/272,634

(22) Filed: Oct. 16, 2002

(65) Prior Publication Data

US 2004/0075813 A1 Apr. 22, 2004

(51) Int. Cl.[7] .............................. A61B 3/14; G06K 9/00
(52) U.S. Cl. ...................................... 351/206; 382/154
(58) Field of Search .................................. 351/200, 205, 351/206, 211, 221; 345/419, 582, 583, 629; 382/154; 396/18; 356/12; 128/922

(56) References Cited

U.S. PATENT DOCUMENTS

| | | | | |
|---|---|---|---|---|
| 5,993,001 A | * | 11/1999 | Bursell et al. | 351/212 |
| 6,224,212 B1 | * | 5/2001 | Noda et al. | 351/206 |
| 6,276,799 B1 | * | 8/2001 | Van Saarloos et al. | 351/206 |
| 6,350,031 B1 | * | 2/2002 | Lashkari et al. | 351/221 |
| 6,496,598 B1 | * | 12/2002 | Harman | 382/154 |
| 6,698,887 B2 | * | 3/2004 | Eikelboom et al. | 351/221 |

FOREIGN PATENT DOCUMENTS

| | | | | |
|---|---|---|---|---|
| JP | 2002034924 A | * | 2/2002 | A61B/3/14 |
| JP | 2002165760 A | * | 6/2002 | A61B/3/14 |

OTHER PUBLICATIONS

*Patent Abstracts of Japan*, Publication No. 05–161607, (Jun. 29, 1993).

* cited by examiner

*Primary Examiner*—Brian L. Casler
*Assistant Examiner*—John R Sanders
(74) *Attorney, Agent, or Firm*—Duane Morris LLP (57) ABSTRACT

Multiple fundus images are obtained and stored in a memory. The images concern a same eye to be examined, but are obtained at different positions relative to the optical axis of the eyeball. An image playback portion repeatedly displays fundus images from the memory, in order at a predetermined time pitch and as obtained from the different positions. This encompasses a stereoscopic range, using display of the images one-by-one.

17 Claims, 7 Drawing Sheets

UNIT FOR OBTAINING AND DISPLAYING FUNDUS IMAGE

BACKGROUND OF THE INVENTION

The present invention relates to a unit for obtaining and displaying fundus image, capable of falsely solidly displaying a fundus image obtained.

A conventional method for three-dimensionally watching a fundus image is that two sheets of fundus images are obtained concerning the same eye to be examined, slightly shifting optical axes of the eye to be examined and a fundus camera from each other, and both two fundus images are arranged in the right and left direction for three-dimensionally watching the fundus images with naked eyes or deflecting glasses.

Skill at some degree is necessary in the method for three-dimensionally watching with naked eyes. Then, many persons can not see well. When deflecting glasses is used, the structure of the unit is made complex, inconveniently. In any method, two sheets of photos should be used together, so the management of the images is complex.

Under this situation, developments of a unit for obtaining and displaying fundus image capable of three-dimensionally watching a fundus image without a skill, and in which the management of the fundus image is easy, are still awaited.

SUMMARY OF THE INVENTION

This invention comprises:

a display;

a means for obtaining fundus image, having an objective;

a memory means for storing a plurality of fundus images concerning the same eye to be examined, obtained through said means for obtaining fundus image, where positional relations between an optical axis of an eyeball of said eye to be examined and an optical axis of said objective are different from each other; and an image playback portion for repeatedly displaying a plurality of said fundus images stored in said memory means, in order at a predetermined time pitch on said display.

According to this invention, the fundus image can be three-dimensionally watched without a skill since a plurality of the fundus images where the positional relation between the optical axis of the eyeball of the eye to be examined and the optical axis of the objective is different from each other concerning the same eye to be examined are repeatedly displayed in order on the display at the pitch of a predetermined time.

The present invention is that photographing data concerning said eye to be examined is stored in said memory means, relating to said fundus image.

According to this invention, the management of the fundus image can be made easy since the photographic data concerning the eye to be examined are stored, relating to the fundus image.

The present invention is that said photographing data is binary typed data.

According to this invention, the management of the data is easier than image data, and the memory capacity can be widely decreased since the photographing data are binary typed data.

The present invention is that said photographing data have an identification number of a subject of examination, examined eye data showing which eye of said subject of examination is examined, and stereo photographing position designation information showing relative positional relation of a plurality of said fundus images.

According to this invention, the photographing data have an identification number of a subject of examination, examined eye data showing which eye of the subject of examination is examined, and stereo photographing position designation information showing relative positional relation of a plurality of the fundus images, thereby the identification of the fundus image is easy and the processing of the fundus image is made easy by referring to the photographing data.

The present invention is that said photographing data have stereo photographing position designation information showing relative positional relation of a plurality of said fundus images, and said image playback portion determines display order of a plurality of fundus images on the basis of said stereo photographing position designation information at the time of displaying a plurality of said fundus images in order.

According to this invention, the display order of a plurality of fundus images is determined on the basis of the stereo photographing position designation information at the time of displaying the fundus images in order, thereby displaying is possible, making the difference between the images displayed in order as small as possible, and the solid image which can be easily watched can be provided.

The present invention further comprises a means for computing and displaying solid image for computing and obtaining three dimensional coordinate data from a plurality of said fundus images stored in said memory means and displaying a three dimensional image or a sectional image on said display.

According to this invention, the fundus image which is easier to be watched can be provided by displaying the three-dimensional image or the sectional image.

The present invention is that an intermediate image producing portion for computing and producing an image of a position of a visual point different from a plurality of said fundus images on the basis of a plurality of said fundus images stored in said memory means as an intermediate image is provided, and said image playback portion repeatedly displays said intermediate image produced by said intermediate image producing portion in order at the pitch of a predetermined time on said display together with a plurality of said fundus images.

According to this invention, the solid image having fine texture can be provided by the intermediate image computed and produced in addition to the fundus image obtained.

The present invention is that photographing data concerning said eye to be examined is captured in said fundus image as image information, and a character recognition means for reading said photographing data concerning said eye to be examined, recognizing said image information with a character recognition is provided.

According to this invention, the photographing data are captured in the fundus image as image information, thereby a conventional fundus camera can be used as it is as the means for obtaining the fundus image. Then, it is convenient.

The present invention is that said image playback portion repeatedly display a plurality of said fundus images in such a manner that a right image and a left image are displayed with a front image as its center as a pendulum.

According to this invention, a plurality of fundus images are displayed in such a manner that a right image and a left image are repeatedly displayed with a front image as its center as a pendulum, thereby the difference between the images displayed in order is made small, and the image having few flickering, which can be easily three-dimensionally watched, can be played back.

DESCRIPTION OF THE PREFERRED EMBODIMENTS

Figure 1:
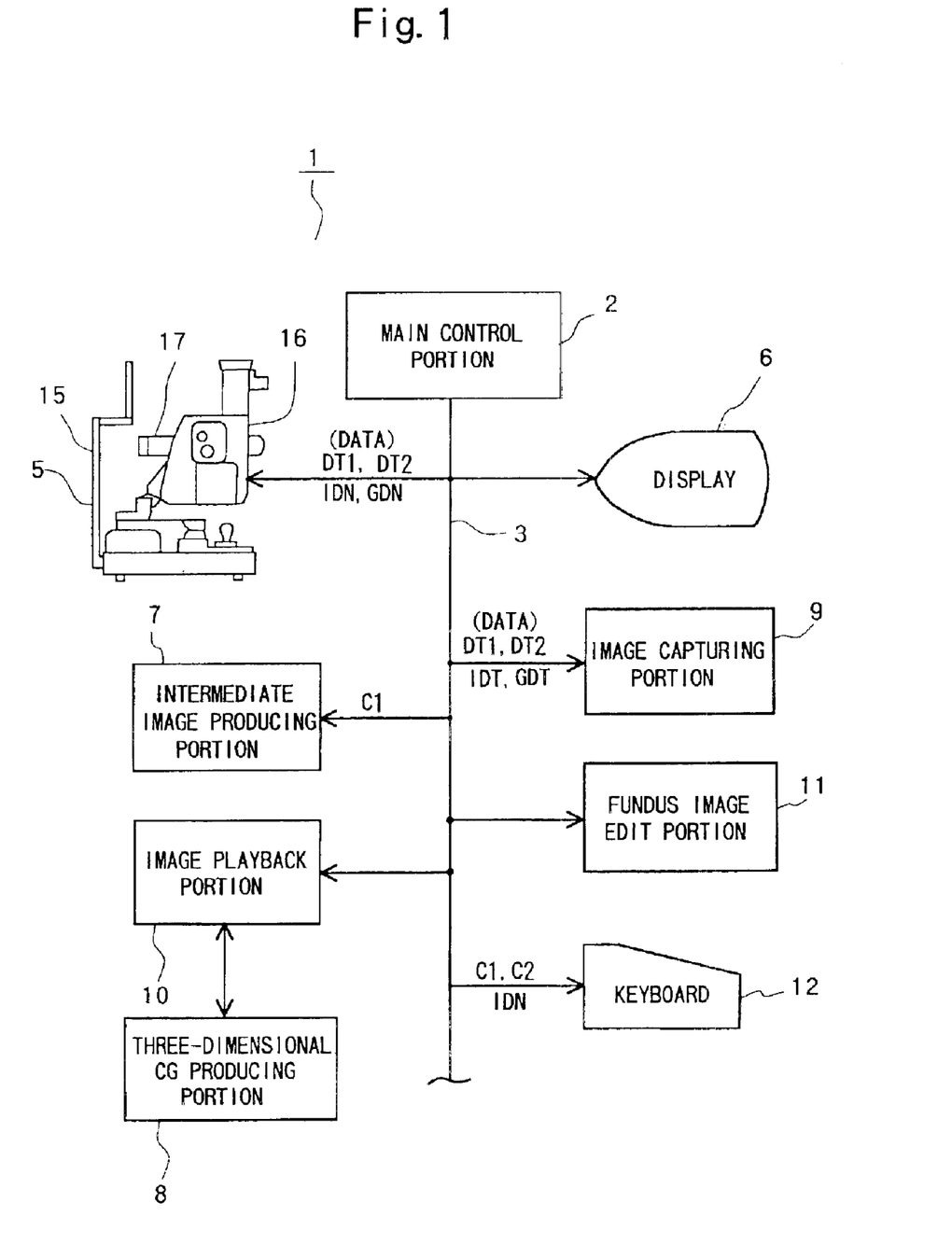
FIG. 1 is a block diagram for showing an example of unit for obtaining and displaying fundus image to which the present invention is applied.

A unit for obtaining and displaying fundus image 1 has a main control portion 2, as shown in FIG. 1, and a fundus camera 5, a display 6, an intermediate image producing portion 7, an image capturing portion 9, an image playback portion 10, a fundus image edit portion 11, a keyboard 12 and the like are connected with the main control portion 2, through a bus line 4. And, a three-dimensionally CG producing portion 8 is connected with the image playback portion 10.

Figure 5:
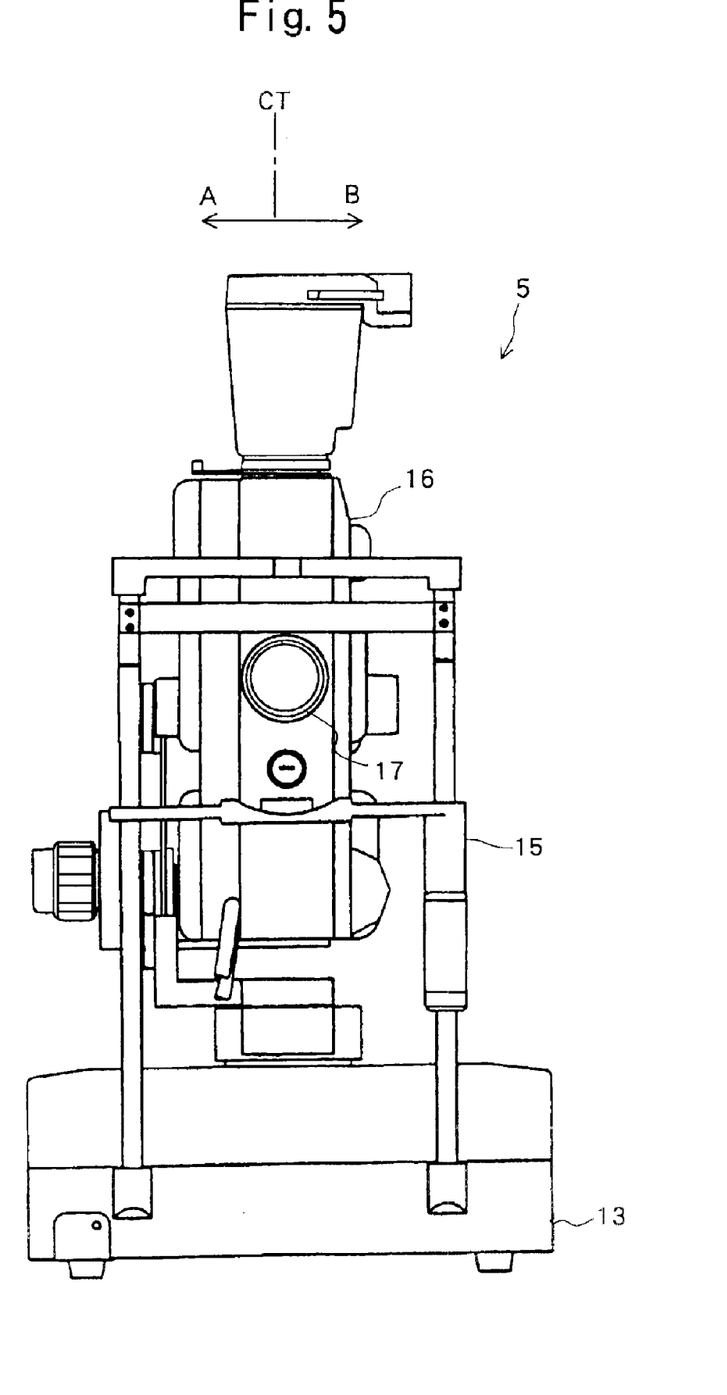
FIG. 5 is a front view for showing an example of the fundus camera.

As shown in FIG. 5, the fundus camera 5 has a base 13, and the base 13 is provided with a jaw support 15, supporting a face of a subject of examination by a camera body. The base 13 is provided with a camera body 16, being free to move within predetermined bounds in a horizontal direction, that is, in a direction as shown by arrows A and B in the figure, and the camera body 16 is provided with an objective 17 so as to face an eye to be examined of a subject.

Figure 2:
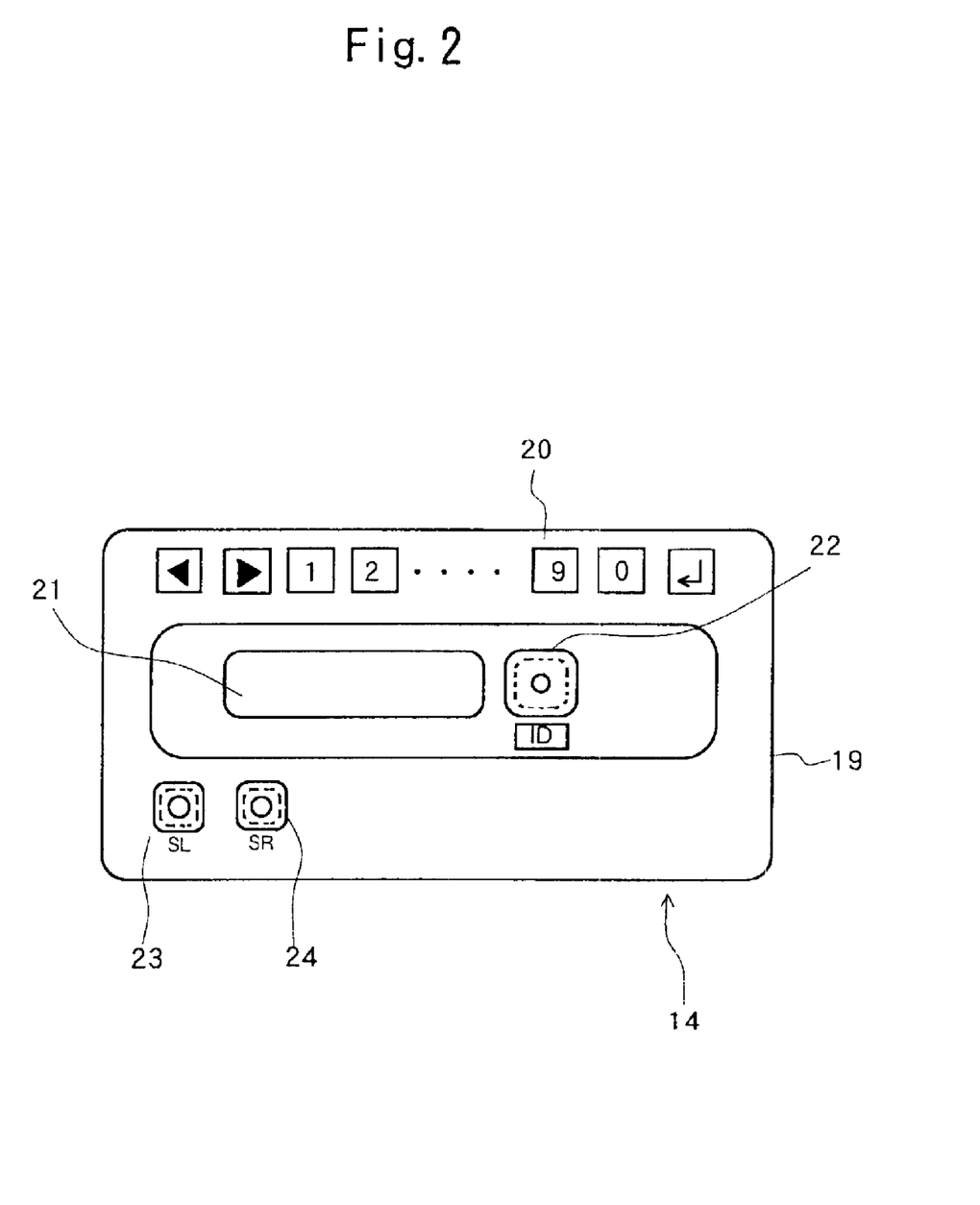
FIG. 2 is a schematic for showing a console panel of a fundus camera.

As shown in FIG. 2, the base 13 is provided with a console panel 14, and the console panel 14 is provided with a ten key 20, a display 21, an ID switch 22, stereo photographing position designation buttons 23, 24 and the like. On this occasion, another many input keys and switches are provided on the console panel 14, but these are not explained, nor shown since these does not directly relate to the present invention.

The unit for obtaining and displaying fundus image 1 has the above-mentioned structure. In order to obtain a fundus photo of a subject of examination with the unit for obtaining and displaying fundus image 1, a jaw of the subject of examination is positioned on the jaw support 15 at first so as to face the eye to be examined and the camera body 16 each other. Subsequently, a tester moves the camera body 16 in the arrow A direction or in the arrow B direction of FIG. 5 so as to face the right eye or the left eye of the subject of examination and the objective 17 of the camera body 16 each other.

In order to obtain the fundus image of the right eye of the subject of examination, the camera body 16 is moved in the direction as shown by the arrow B with respect to a center position CT in its right and left direction, and in order to obtain the fundus image of the left eye of the subject of examination, the camera body 16 is moved in the direction as shown by the arrow A with respect to the center position CT of the right and left direction, as shown in FIG. 5. Then, the tester can immediately perceive to which eye of both right and left eyes the fundus image to be obtained by the fundus camera 5 from now on relates by detecting the moving form of the camera body 16 with respect to the center position CT with a proper means, such as a sensor.

Figure 3:
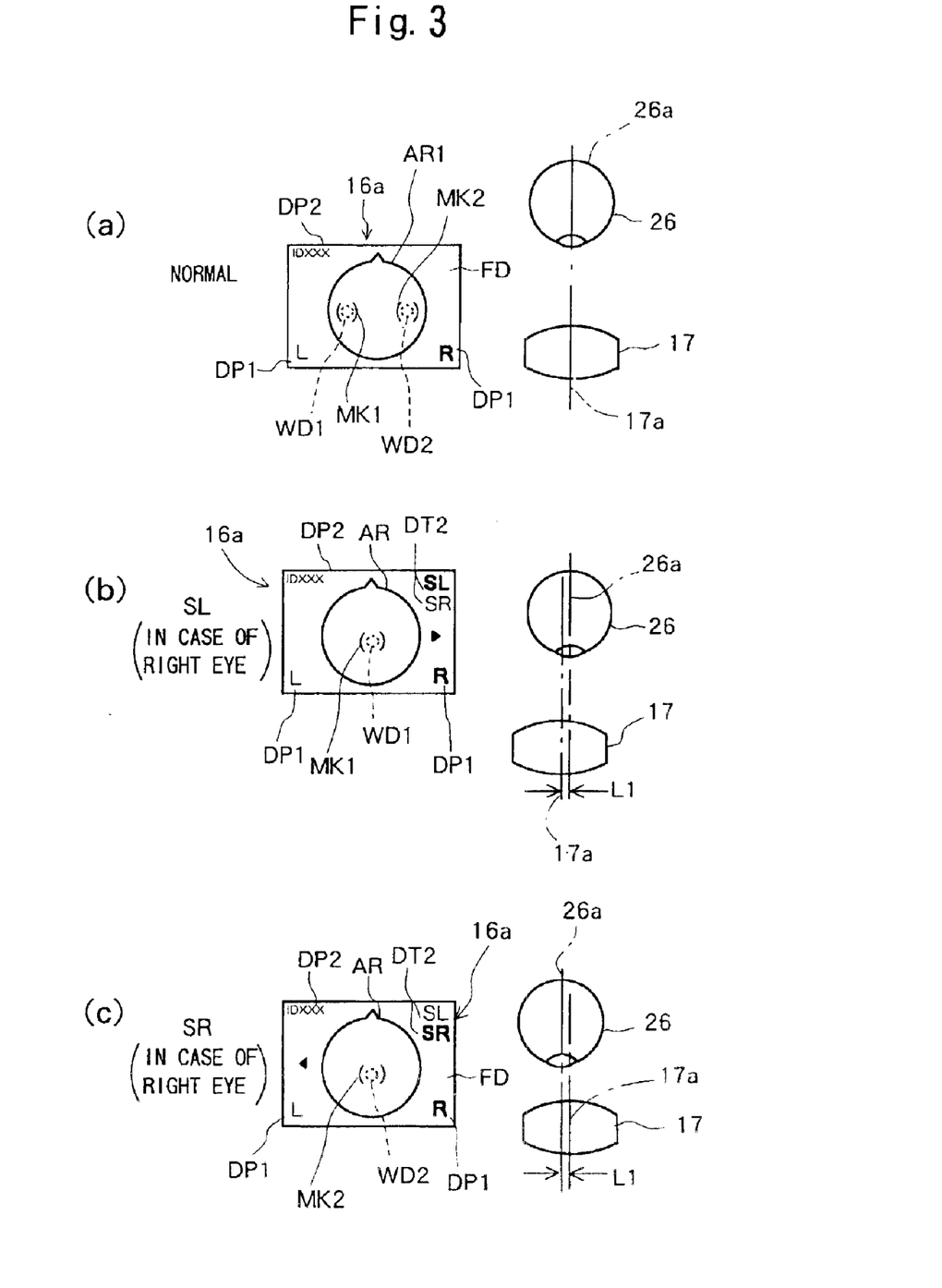
FIGS. 3(a), 3(b) and 3(c) are views for showing a relation between optical axes of an eye to be examined and an objective at the time of obtaining fundus image and a finder image at this time.

Examined eye data DT1 showing the right or the left of the eye to be examined, which is judged on the basis of the position with respect to the center position CT of the camera body 16 detected by a sensor, are output to the image capturing portion 9, and for instance, "R" showing right eye of the indication of "R" showing right eye and "L" showing left eye of right and left examined eye indication DP1 of a visual field FD in a finder 16a of the camera body 16 is displayed with a bold character as shown in FIG. 3 so as to show that the fundus image to be obtained from now on is the image concerning the right eye of a subject of examination.

When a normal fundus photo of a subject of examination is obtained with the fundus camera 5, a tester presses a button (not shown), for instructing to obtain a normal fundus photo, of the console panel 14 so as to input obtaining a normal fundus photo from now on to the fundus camera 5. Then, an indication DP2 for inputting an identification number of a subject of examination flashes in the visual field FD so as to be requested to input the identification number of the subject of examination through the ten key 20 or the like.

Then, the tester presses the ID switch 22 of the console panel 14, and inputs an identification number TDN of the subject of examination by operating the ten key 20. Then, the input identification number IDN is displayed on the indication DP2 in the visual field FD, and is notified the image capturing portion 9.

In case of a normal fundus photo, it is necessary to obtain the fundus image in such a state that an optical axis 26a of an eyeball 26 and an optical axis 17a of the objective 17 correspond with each other, as shown in FIG. 3(a). In order to do so, positioning marks MK1, MK2 for positioning are displayed on both right and left sides in a circular pixel obtaining area AR1 where the fundus photo should be obtained, and two light spots WD1, WD2 for positioning which are provided respectively corresponding to both positioning marks MK1, MK2 are displayed in the visual field FD of the fundus camera 5. Then, the tester slightly moves the camera body 16 in the direction as shown by the arrows A and B and in the up and down direction of FIG. 5 so that both spot lights WD1, WD2 can enter in the positioning marks MK1, MK2, and positions the camera body 16 so that the optical axis 26a of the eyeball 26 and the optical axis 17a of the objective 17 can correspond with each other. On this occasion, the method of correspondence between the optical axis 26a of the eyeball 26 and the optical axis 17a of the objective 17 using the positioning marks MK1, MK2 and the spot lights WD1, WD2 is a well known method. So, its detailed explanation is omitted.

When the optical axis 26a of the eyeball 26 and the optical axis 17a of the objective 17 are corresponded with each other, the beam for photographing, such as flash beam, is projected to the eyeball 26 from the camera body 16 so as to obtain the fundus image. A fundus front image SFV obtained, corresponding the optical axis 26a of the eyeball 26 and the optical axis 17a of the objective 17 with each other, is output to the image capturing portion 9 as fundus image data GDT. On this occasion, "front image" of a fundus in the present specification means the fundus image photographed corresponding the optical axis 26a of the eyeball 26 and the optical axis 17a of the objective 17 with each other, "left image" means the fundus image photographed in such a state that the optical axis 17a of the objective 17 is shifted on the left side with respect to the optical axis 26a of the eyeball 26, and "right image" means the fundus image photographed in such a state that the optical axis 17a of the objective 17 is shifted on the right side with respect to the optical axis 26a of the eyeball 26.

In case where the fundus image to be obtained from now on is a stereo image, the tester inputs the above-mentioned identification number IDN, and thereafter, and presses the stereo photographing position designation button 23 indicating "SL" in FIG. 2 of the console panel 14.

Then, the fundus camera 5 enters in a stereo left photographing mode. This stereo left photographing mode is the mode to be photographed in such a state that the optical axis 17a of the objective 17 is shifted a slight length L1 on the left side with respect to the optical axis 26a of the eyeball 26, as shown in FIG. 3(b).

When the stereo photographing position designation button 23 is pressed, an indication "SL" showing that the fundus image to be obtained from now on is the left side image of the stereo image is displayed with bold characters in the visual field FD of the finder 16a as shown in FIG. 3(b), and stereo photographing position designation information DT2 which is "SL" for instance are output to the image capturing portion 9. At the time of obtaining a normal fundus image, that is, the fundus front image SFV, corresponding the optical axis 26a of the eyeball 26 and the optical axis 17a of the objective 17 with each other, the stereo photographing position designation information DT2 is no designation state, for instance "0".

In this stereo left photographing mode, only positioning mark MK1 for positioning is displayed in the center of the circular pixel obtaining area AR1 where the fundus image should be obtained in the visual field FD of the fundus camera 5. That is, the positioning mark MK1 which has been located on the left side in the pixel obtaining area AR1 is located in the center in the case of photographing with corresponding between the optical axis 26a of the eyeball 26 and the optical axis 17a of the objective 17. Then, the tester slightly moves the camera body 16 in the direction as shown by the arrows A and B and in the up and down direction of FIG. 5 so that the corresponding spot light WD1 for positioning can enter in the positioning mark MK1. Then, the camera body 16 is positioned in such a state that the optical axis 17a of the objective 17 is shifted a slight length L1 on the left side with respect to the optical axis 26a of the eyeball 26.

In this way, it is sufficient for the tester to only adjust the position of the camera body 16 so that the spot light WD1 for positioning can enter in the corresponding positioning mark MK1, and extremely easy positioning is possible.

When the camera body 16 is positioned in such a state that the optical axis 17a of the objective 17 is shifted the slight length L1 on the left side with respect to the optical axis 26a of the eyeball 26 in this way, the beam for photographing, such as flash beam, is projected to the eyeball 26 from the camera body 16 so as to obtain a stereo fundus left image SLV. The stereo fundus left image SLV obtained in this way is output to the image capturing portion 9 as the fundus image data GDT.

Subsequently, the tester presses the stereo photographing position designation button 24 showing "SR" in FIG. 2 of the console panel 14.

Then, the fundus camera 5 enters in a stereo right photographing mode. This stereo right photographing mode is the mode to be photographed in such a state that the optical axis 17a of the objective 17 is shifted a slight length L1 on the right side with respect to the optical axis 26a of the eyeball 26, as shown in FIG. 3(c).

When the stereo photographing position designation button 24 is pressed, an indication "SR" showing that the fundus image to be obtained from now on is the right side image of the stereo image is displayed with bold characters in the visual field FD of the finder 16a as shown in FIG. 3(c), and stereo photographing position designation information DT2 which is "SR" for instance are output to the image capturing portion 9.

In this stereo right photographing mode, only positioning mark MK2 for positioning is displayed in the center of the circular pixel obtaining area AR1 where the fundus image should be obtained in the visual field FD of the fundus camera 5. That is, the positioning mark MK2 which has been located on the right side in the pixel obtaining area AR1 is located in the center in the case of photographing with corresponding between the optical axis 26a of the eyeball 26 and the optical axis 17a of the objective 17. Then, the tester slightly moves the camera body 16 in the direction as shown by the arrows A and B and in the up and down direction of FIG. 5 so that the corresponding spot light WD2 for positioning can enter in the positioning mark MK2. Then, the camera body 16 is positioned in such a state that the optical axis 17a of the objective 17 is shifted the slight length L1 on the right side with respect to the optical axis 26a of the eyeball 26.

In this way, it is sufficient for the tester to only adjust the position of the camera body 16 so that the spot light WD2 for positioning can enter in the corresponding positioning mark MK2, and extremely easy positioning is possible.

When the camera body 16 is positioned in such a state that the optical axis 17a of the objective 17 is shifted the slight length L1 on the right side with respect to the optical axis 26a of the eyeball 26 in this way, the beam for photographing, such as flash beam, is projected to the eyeball 26 from the camera body 16 so as to obtain a stereo fundus right image. A stereo fundus right image SRV obtained in this way is output to the image capturing portion 9 as the fundus image data GDT.

On this occasion, the stereo fundus left image SLV and the stereo fundus right image SRV which are output to the image capturing portion 9 may be output in such a manner that not only fundus image but also the indication DP2 of the identification number IDN of a subject of examination or the indication "SL" or "SR" of the stereo photographing position designation information DT2, which are shown in the visual field FD of the finder 16a, is captured as image information together with the fundus image.

Photographing data DATA captured by the image capturing portion 9, such as the examined eye data DT1, the identification number IDN, and the stereo photographing position designation information DT2 concerning some eye to be examined are stored in a predetermined memory area as binary data in this way. On this occasion, the fundus image edit portion 11 edits the photographing data DATA stored and the fundus image data GDT, such as the stereo fundus left image SLV and the stereo fundus right image SRV, relating to each other so as to store in a predetermined memory area. This is the same in the case of the fundus front image SFV.

That is, when some fundus image data GDT are read out of the memory area, the corresponding photographing data DATA are also immediately read out so as to identify the fundus image data GDT. On the contrary, the photographing data are input, thereby the corresponding fundus image data GDT are also retrieved so as to read out. When the fundus image data GDT are not only fundus image, but the indication DP2 of the identification number IDN of a subject of examination or the indication "SL or "SR" of the stereo photographing position designation information DT2, which is shown in the visual field FD of the finder 16a, is captured in the fundus image data GDT as image information together with the fundus image, the corresponding photographing data DATA are immediately known on the image by only reading out the fundus image data GDT. Then, it is convenient. When the photographing data DATA are stored as binary data so as to own as mentioned before, the binary data can be also immediately utilized by an another electronic inspection appliance. Besides, the photographing data DATA on the image are converted into binary information using a well-known character recognition means so that each fundus image data GDT can be pigeonholed and stored. In this case, it is not necessary to output the photographing data DATA in addition to the fundus image data GDT from the fundus camera 5 side, and data transfer time can be shortened. Because the fundus image data GDT in which the photographing data DATA are copied is output to the image capturing portion 9 from the fundus camera 5 side so that the image capturing portion 9 reads the photographing data DATA out of the fundus image data GDT by character recognition, and stores in the memory means, relating to the fundus image data GDT.

When the stereo fundus left image SLV, the stereo fundus right image SRV, and furthermore, the normal fundus front image SFV photographed in such a state that the optical axis 26a of the eyeball 26 and the optical axis 17a of the objective 17 correspond with each other are obtained, concerning some eye to be examined so as to be stored in a predetermined memory area in this way, a doctor operates the unit for obtaining and displaying fundus image 1 at a proper time, such as a informed consent to the subject of examination so as to play back the fundus image data GDT on the display 6. On this occasion, a doctor inputs an image playback instruction C2 and the identification number IDN of a subject of examination through the keyboard 12. Receiving this, the main control portion 2 instructs the image playback portion 10 to read out and play back the fundus image data GDT related to the identification number IDN.

That is, the image playback portion 10 reads the stored fundus image data GDT corresponding to the identification number IDN out of the image capturing portion 9 so as to output to the display 6. On this occasion, the image playback portion 10 gets the display 6 to repeatedly display a plurality of fundus image data GDT attaching the same identification number TDN thereon in order every predetermined time (for instance, every 1 or 2 seconds).

Then, for instance, the stereo fundus left image SLV is first displayed, the fundus front image SFV is subsequently displayed (in case where the fundus front image SFV has been obtained), the stereo fundus right image SRV is subsequently displayed, the fundus front image SFV is again displayed, and the stereo fundus left image SLV is further displayed on the display 6 concerning some eye to be examined. That is, continuous display cycle is executed. In other words, the images in right and left direction (including an intermediate synthetic image described hereinafter) are repeatedly played back and displayed in order with the front image as its center as a pendulum, such as the front image→the right image→the front image→the left image→the front image→the right image→the front image→the left image→the front image concerning the same eye to be examined.

On this occasion, the display order of each image is optional, and such display form that the stereo fundus left image SLV and the stereo fundus right image SRV are alternately displayed with the fundus front image SFV as its center is also of course possible. But, desirably, both images are displayed, making the shift quantity of the optical axis 26a of the eyeball 26 and the optical axis 17a of the objective 17 between both images continuously displayed as few as possible in order to prevent the flickering of the image and to represent natural real existence having depth. Such control of the display order is executed by the image playback portion 10 on the basis of the stereo photographing position designation information DT2, showing relative positional relation among a plurality of fundus images.

Then, the person who sees the image continuously sees the fundus images obtained with slightly different visual point, and the person feels as if the solid image was displayed on the display 6, and it becomes easy to understand the fundus image.

If necessary, an intermediate image producing instruction C1 can be also output to the intermediate image producing portion 7 from the keyboard 12 so as to compute and produce the image of the intermediate view point position of a plurality of images SLV, SRV and SFV, comprising the fundus image data GDT stored in a memory from these images as an intermediate image MV. The intermediate image MV produced is squeezed in the above-mentioned display cycle so as to display by the image playback portion 10 at the time of the playback of the fundus image data GDT. By doing so, more natural solid image can be displayed.

Figure 4:
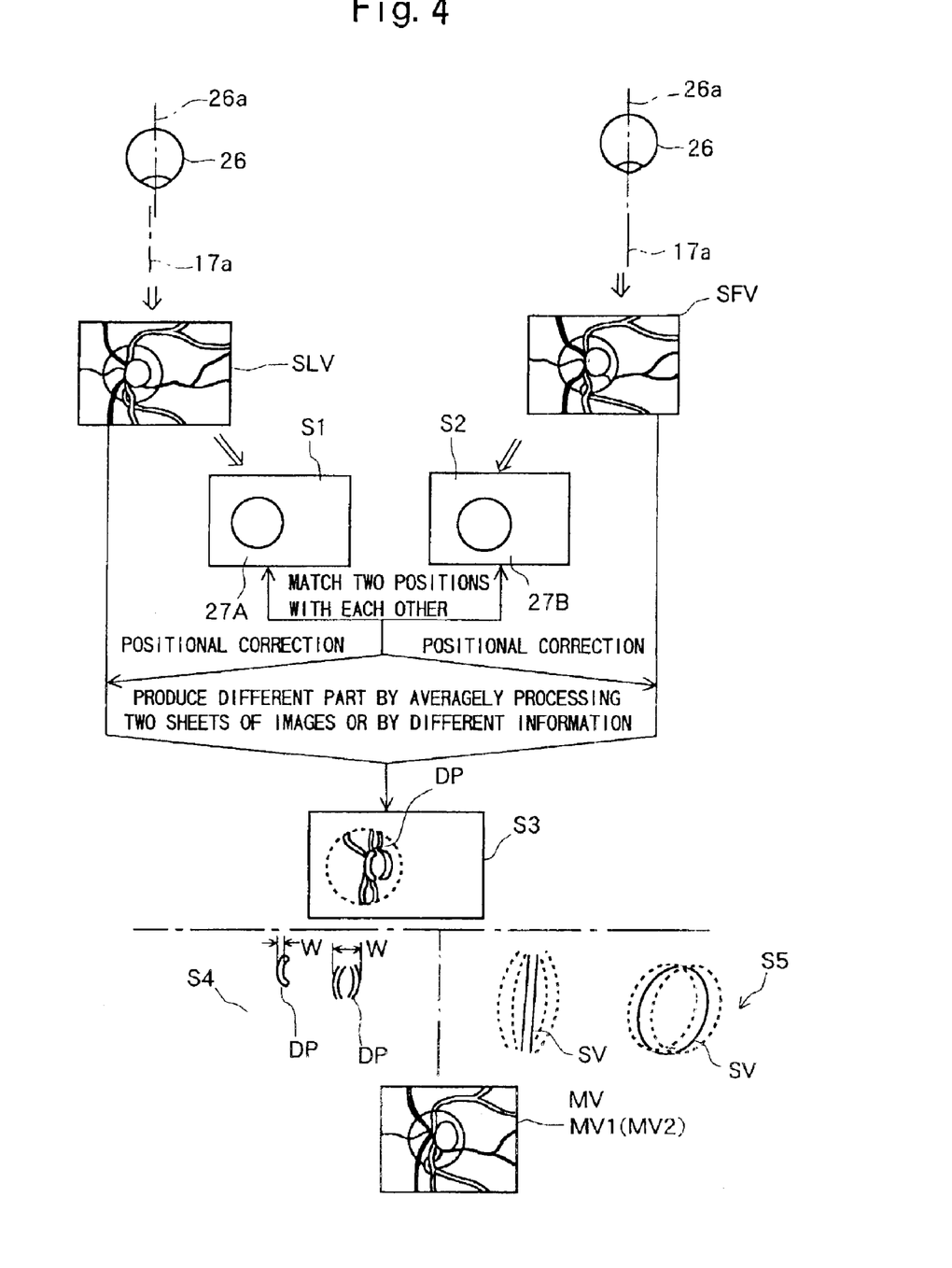
FIG. 4 is a view for showing a routine of producing an intermediate image.

As a method for producing the intermediate image, the simple method of using mean image of two images or another various kinds of image processing methods can be used. An instance of these will now be explained, referring to FIG. 4. The image processing of FIG. 4 shows the method for obtaining the intermediate image MV of the stereo fundus left image SLV and the fundus front image SFV using these images. In Step S1 and Step S2, optic disk portions 27A, 27B are first drawn out of the both images SLV, SFV on the basis of color difference information.

Subsequently, the positions of both images SLV and SFV are matched with each other on the basis of the optic disk portions 27A, 27B drawn out so as to correct the positions of both images by detecting the place where the sum of the difference of gradation of both images is the smallest. By this processing, both images SLV and SFV are correctly corresponded to each other concerning the position of the up and down direction and the right and left direction of the scope on the basis of the optic disk portions 27A, 27B.

When both images SLV, SFV are averagely processed or the difference of both images is obtained, only different part DP of both images SLV, SFV is drawn out, as shown in Step S3. Then, width W of the respective different parts DP in the horizontal direction is obtained in Step S4. Subsequently, a newly shifted image SV is produced at the intermediate position of the width W obtained in Step S4 on the basis of the different part DP, and the image SV produced is inserted into the image SLV or SFV so as to produce a new intermediate image MV1 in Step S5.

A similar intermediate image MV2 is also produced between the fundus front image SFV and the stereo fundus right image SRV.

The image playback portion 10 repeatedly plays back the stereo fundus left image SLV, the intermediate image MV1, the fundus front image SFV, the intermediate image MV2, the stereo fundus right image SRV, the intermediate image MV2, the fundus front image SFV, the intermediate image MV1 and the stereo fundus left image SLV every predetermined time in this order, making use of the produced intermediate image MV (MV1, MV2) so that solid image having fine texture can be displayed.

On this occasion, three dimensional coordinate data can be also computed and obtained from a plurality of the fundus image data GDT photographed in such a state that the positional relation between the optical axis 26*a* of the eyeball 26 and the optical axis 17*a* of the objective 17 is different by a well-known method by the image playback portion 10 through the three-dimensional CG producing portion 8 so as to display the three dimensional image or the sectional image on the display 6.

Figure 6:
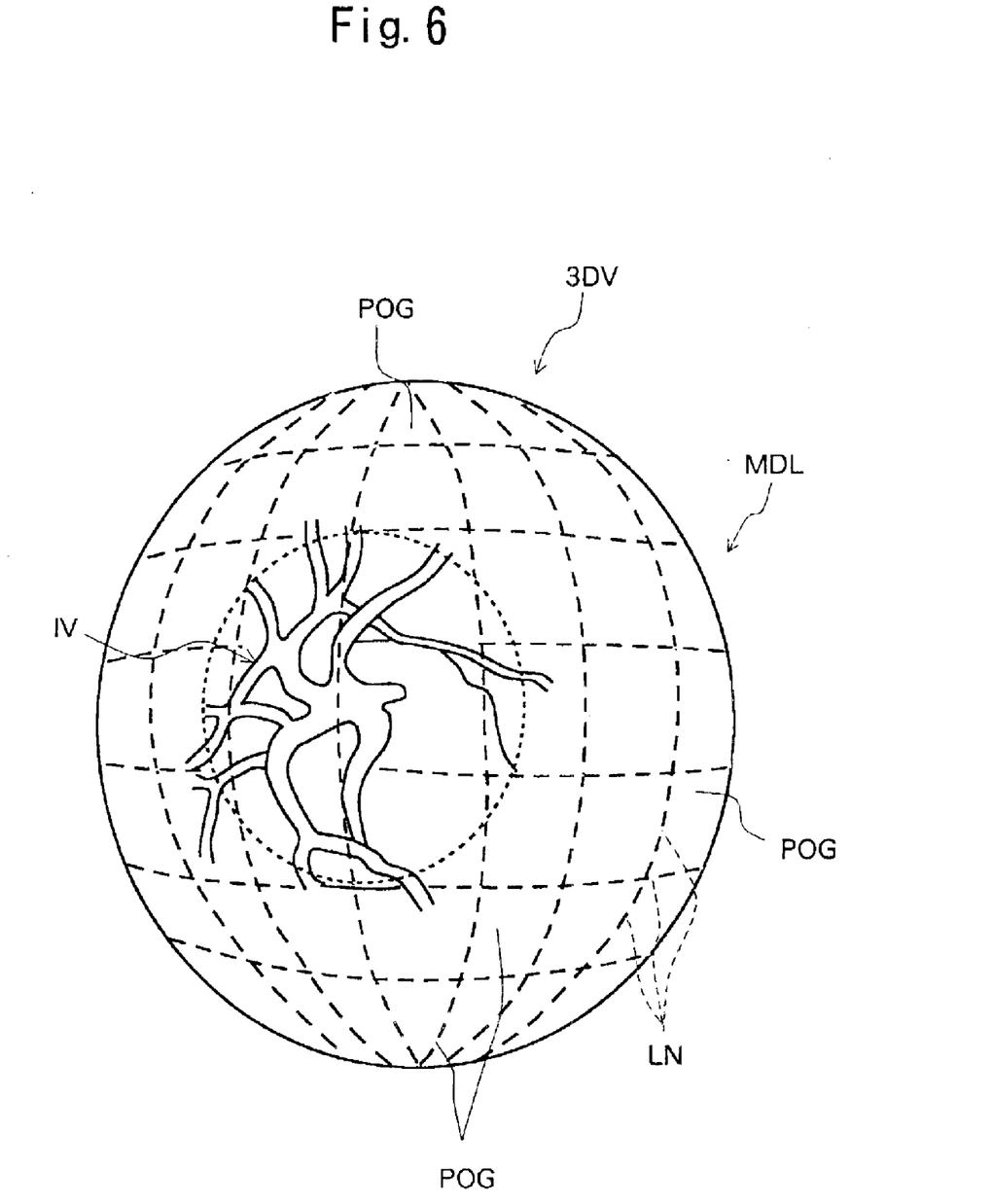
FIG. 6 is an example of the obtained fundus image shown by three-dimensional computer graphics.

And, the three-dimensional CG producing portion 8 respectively maps fundus images IV, such as the stereo fundus left image SLV, the intermediate image MV1, the fundus front image SFV, the intermediate image MV2, and the stereo fundus right image SRV, on a well known three-dimensional fundus model MDL (only fundus part is available) in a three-dimensional virtual space, using computer graphic technique so that a solid image 3DV as shown in FIG. 6 can be produced and the produced solid image 3DV can be displayed on the display 6 through the image playback portion 10. FIG. 6 is an example of the solid image 3DV obtained by mapping the fundus front image SFV on the three-dimensional fundus model MDL. The rate of permeation of the three-dimensional fundus model MDL should be set in a transparent state excluding a boundary LN showing the outer periphery of each polygon POG, so that the three-dimensional fundus model MDL can be rendered from the outside of the model. On this occasion, it is not always to map all of the fundus images obtained by the camera body 16 as the fundus image IV for mapping on the three-dimensional fundus model MDL, but fundus images properly selected can be also used in case of necessity.

A plurality of the solid images 3DV produced in this way are repeatedly played back in the order of the stereo fundus left image SLV, the intermediate image MV1, the fundus front image SFV, the intermediate image MV2 and the stereo fundus right image SRV which are mapped on the display 6 every predetermined time as mentioned above, thereby more solid image can be displayed. On this occasion, a size of the solid image 3DV, a position of rendering, that is, the angle of displaying the solid image 3DV on the display 6 can be optionally adjusted and set by an instruction of an operator through the keyboard 12.

Figure 7:
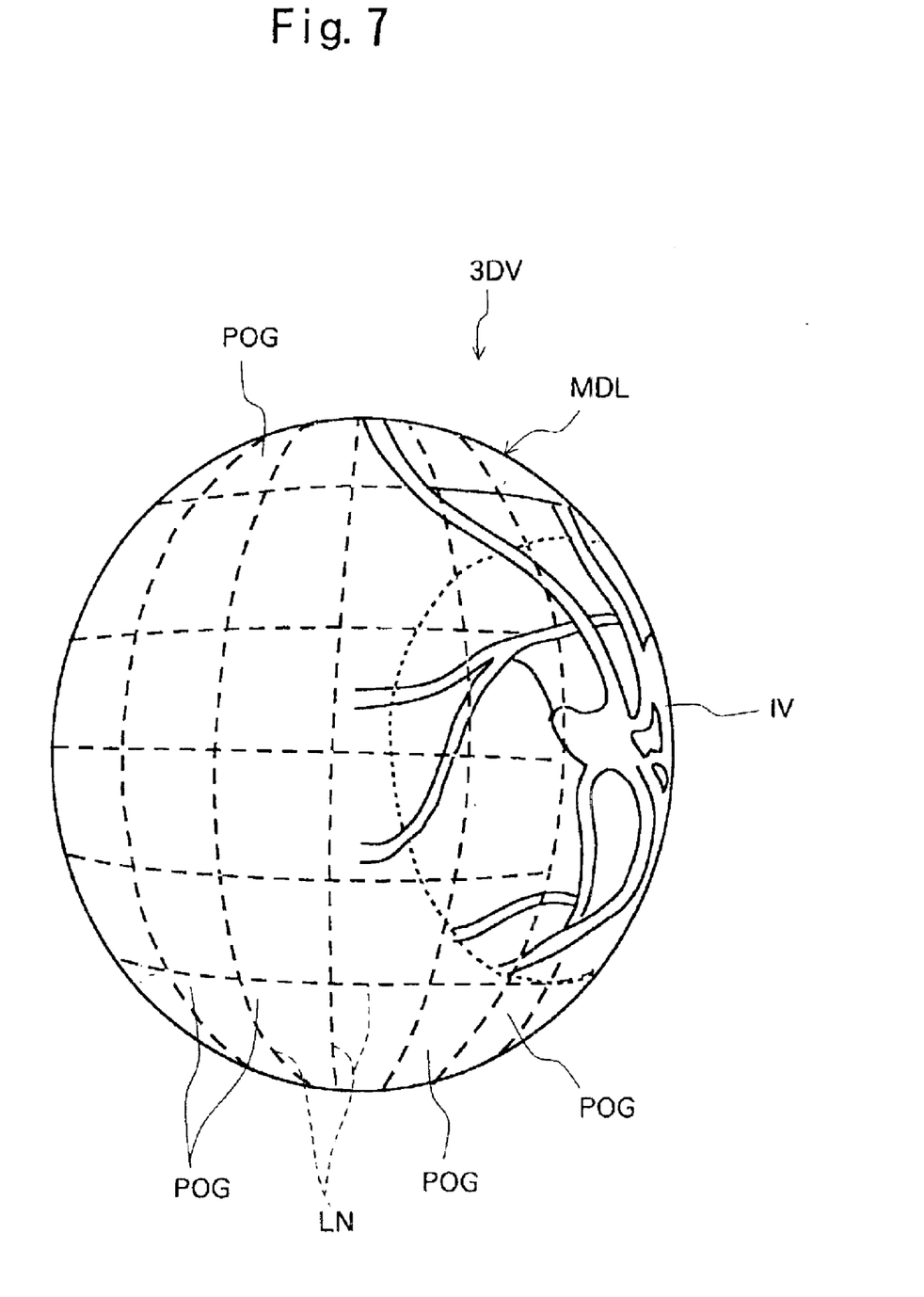
FIG. 7 is an example of the obtained fundus image shown by three-dimensional computer graphics.

Furthermore, the three-dimensional fundus model MDL on which the fundus image is mapped is rendered at an optional position in the three-dimensional virtual space, thereby the solid image 3DV seen from the back can be also easily displayed, as shown in FIG. 7 for instance. Besides, the three-dimensional fundus model MDL, on which the stereo fundus left image SLV, the intermediate image MV1, the fundus front image SFV, the intermediate image MV2 and the stereo fundus right image SRV are respectively mapped, is rendered at the same position and is repeatedly played back on the display 6 every predetermined time as mentioned before, thereby a solid image from a different view point can be also displayed.

On this occasion, the image playback portion 10 can also display the polygons POG comprising the three-dimensional fundus model MDL on the display together with the mapped fundus images for easy understanding of the solid image 3DV by an instruction of an operator through the keyboard, as shown in FIG. 6 and FIG. 7. And, it is off course possible not to display the polygon POG in order to detailedly watch the solid image 3DV.

The present invention is explained on the basis of the embodiment heretofore. The embodiments which are described in the present specification are illustrative and not limiting. The scope of the invention is designated by the accompanying claims and is not restricted by the descriptions of the specific embodiments. Accordingly, all the transformations and changes belonging to the claims are included in the scope of the present invention.

What is claimed is:

1. Unit for obtaining and displaying fundus image, comprising:
    a display;
    a means for obtaining fundus image, having an objective;
    a memory means for storing a plurality of fundus images concerning the same eye to be examined, obtained through said means for obtaining fundus image, where positional relations between an optical axis of an eyeball of said eye to be examined and an optical axis of said objective are different from each other, whereby the plurality of images encompass a stereoscopic range; and
    an image playback portion for repeatedly displaying one-by-one a plurality of said fundus images stored in said memory means, in order at a predetermined time pitch on said display, thereby displaying the stereoscopic range.

2. The unit for obtaining and displaying fundus image according to claim 1, wherein photographing data concerning said eye to be examined is stored in said memory means, relating to said fundus image.

3. The unit for obtaining and displaying fundus image according to claim 2, wherein said photographing data is binary typed data.

4. The unit for obtaining and displaying fundus image according to claim 2, wherein said photographing data have an identification number of a subject of examination, examined eye data showing which eye of said subject of examination is examined, and stereo photographing position designation information showing relative positional relation of a plurality of said fundus images.

5. The unit for obtaining and displaying fundus image according to claim 2, wherein said photographing data have stereo photographing position designation information showing relative positional relation of a plurality of said fundus images, and said image playback portion determines display order of a plurality of fundus images on the basis of said stereo photographing position designation information at the time of displaying a plurality of said fundus images in order.

6. The unit for obtaining and displaying fundus image according to claim 1, further comprising a means for computing and displaying a solid image for computing and obtaining three dimensional coordinate data from a plurality of said fundus images stored in said memory means and displaying a three dimensional image or a sectional image on said display.

7. The unit for obtaining and displaying fundus image according to claim 1, wherein an intermediate image producing portion for computing and producing an image of a position of a visual point different from a plurality of said fundus images on the basis of a plurality of said fundus images stored in said memory means as an intermediate image is provided, and said image playback portion repeatedly displays said intermediate image produced by said intermediate image producing portion in order at the pitch of a predetermined time on said display together with a plurality of said fundus images.

8. The unit for obtaining and displaying fundus image according to claim 1, wherein photographing data concerning said eye to be examined is captured in said fundus image as image information, and a character recognition means for reading said photographing data concerning said eye to be examined, recognizing said image information with a character recognition is provided.

9. The unit for obtaining and displaying fundus image according to claim 1, wherein said image playback portion repeatedly display a plurality of said fundus images in such a manner that a right image and a left image are displayed with a front image as its center as a pendulum.

10. Unit for obtaining and displaying fundus image, comprising:
   a display;
   a means for obtaining fundus image, having an objective;
   a memory means for storing a plurality of fundus images concerning the same eye to be examined, obtained through said means for obtaining fundus image, where positional relations between an optical axis of an eyeball of said eye to be examined and an optical axis of said objective are different from each other, whereby the plurality of images encompass a stereoscopic range;
   a three-dimensional CG producing portion for producing a solid image by mapping said fundus image stored in said memory means on a three-dimensional eyeball model in a three-dimensional virtual space; and
   an image playback portion for repeatedly displaying one-by-one said solid images corresponding to said fundus image produced by said three-dimensional CG producing portion, in order at a predetermined time pitch on said display, thereby displaying the stereoscopic range.

11. The unit for obtaining and displaying fundus image according to claim 10, wherein photographing data concerning said eye to be examined is stored in said memory means, relating to said fundus image.

12. The unit for obtaining and displaying fundus image according to claim 11, wherein said photographing data is binary typed data.

13. The unit for obtaining and displaying fundus image according to claim 11, wherein said photographing data have an identification number of a subject of examination, examined eye data showing which eye of said subject of examination is examined, and stereo photographing position designation information showing relative positional relation of a plurality of said fundus images.

14. The unit for obtaining and displaying fundus image according to claim 10, wherein said photographing data have stereo photographing position designation information showing relative positional relation of a plurality of said fundus images, and said image playback portion determines display order of said solid images on the basis of said stereo photographing position designation information at the time of displaying said solid image corresponding to said fundus image in order.

15. The unit for obtaining and displaying fundus image according to claim 10, wherein an intermediate image producing portion for computing and producing an image of a position of a visual point different from a plurality of said fundus images on the basis of a plurality of said fundus images stored in said memory means as an intermediate image is provided, said three-dimensional CG producing portion produces said solid image by also mapping said intermediate image produced by said intermediate image producing portion on said three-dimensional eyeball model in said three-dimensional virtual space, and said image playback portion repeatedly displays said solid image corresponding to said intermediate image in order at the pitch of a predetermined time on said display together with said solid images corresponding to a plurality of said fundus images.

16. The unit for obtaining and displaying fundus image according to claim 10, wherein photographing data concerning said eye to be examined is captured in said fundus image as image information, and a character recognition means for reading said photographing data concerning said eye to be examined, recognizing said image information with a character recognition is provided.

17. The unit for obtaining and displaying fundus image according to claim 10, wherein said image playback portion repeatedly displays said solid images corresponding to a plurality of said fundus images in order in such a manner that said solid images respectively corresponding to a right image and a left image are displayed with said solid image corresponding to a front image as its center as a pendulum.

* * * * *